US00PP26951P2

(12) United States Plant Patent
Kordes

(10) Patent No.: US PP26,951 P2
(45) Date of Patent: Jul. 19, 2016

(54) FLORIBUNDA ROSE PLANT NAMED 'KORANGOBER'

(50) Latin Name: *Rosa hybrida*
Varietal Denomination: KORangober

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 91 days.

(21) Appl. No.: 14/120,935

(22) Filed: Jul. 11, 2014

(51) Int. Cl.
*A01H 5/02* (2006.01)

(52) U.S. Cl.
USPC ..... Plt./145

(58) Field of Classification Search
USPC ..... Plt./145
See application file for complete search history.

(56) References Cited

PUBLICATIONS

Dave's Garden, Floribunda Rose 'Sweet Jane', http://davesgarden.com/guides/pf/go/222743/#b, 1999.*

* cited by examiner

*Primary Examiner* — Anne Grunberg

(57) ABSTRACT

A new and distinct variety of rose with long lasting, novel apricot flowers, and attractive foliage with very good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORangober'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1999. The crossing was between an un-named seedling, the seed parent, and an un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORangober'.

SUMMARY OF THE INVENTION

The new rose plant may be distinguished from its seed parent, an un-named seedling, by the following combination of characteristics:

1. 'KORangober' has a very double petal count, whereas the un-named seedling has a semi-double petal count.

2. 'KORangober' has large sized flowers, whereas the un-named seedling has small sized flowers.

The new rose plant may be distinguished from its pollen parent, an un-named seedling, by the following combination of characteristics:

1. 'KORangober' has a bushy growth habit, whereas the un-named seedling has an upright growth habit.
2. 'KORangober' has apricot-colored flowers, whereas the un-named seedling has yellow flowers.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORangober' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORangober' was selected in May 2000 from the seedling beds to be asexually propagated for further evaluation. The first asexual propagation of 'KORangober' was done by budding in July 2000 at the inventor's nursery in Offenseth-Sparrieshoop, Germany.

These initial and other subsequent propagations conducted in controlled environments demonstrate that 'KORangober' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORangober'.

DETAILED BOTANICAL DESCRIPTION

The following is a description of 'KORangober', as observed growing in May 2014 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORquelda', a rose variety from the same inventor described and illustrated in U.S. Plant Pat. No. 17,048 issued on Aug. 22, 2006 are compared to 'KORangober' in Chart 1.

CHART 1

| Characteristic | 'KORangober' | 'KORquelda' |
|---|---|---|
| Average Open Flower Diameter. | 85 to 90 mm. | 60 to 70 mm. |
| General Tonality of Open Flower. | Yellow-Orange Group 27C. | Yellow Group 5A. |
| Petal Count | Approximately 80 to 90 petals. | Approximately 40 petals. |

Parents:

*Seed parent*.—An un-named seedling.

*Pollen parent*.—An un-named seedling.

Classification:

*Botanical classification*.—*Rosa hybrida* 'KORangober'.

*Commercial classification*.—Floribunda rose.

FLOWER AND FLOWER BUD

Blooming habit: Recurrent. Floriferous.

Flower bud:

*Size*.—Upon opening, 45-50 mm in length from base of receptacle to distal end of bud and 35-40 mm diameter at its widest point.

*Bud form*.—Globular.

*Bud color*.—As sepals first unfold, bud color is Orange Group 24B. When ¼ open, the upper surface of petals is Yellow-Orange Group 16B, and the lower surface is Orange Group 26B.

*Sepals*.—Color: Upper surface Yellow-Green Group 147C. Lower surface Yellow-Green Group 146B with intonations of Greyed-Purple Group 183C. Size: Average 35 mm (l)×14 mm (w). Shape: Weak foliaceous appendages on 3 of the five sepals. Apex: Apiculate. Base: Flat at union with receptacle. Quantity: Five. Surface texture: Upper side: Pubescent. Lower surface: Leathery. Margins: Pubescent with stipitate glands present. Stipitate glands: Present on lower surface and margins.

Flower bloom:

*Fragrance*.—Light.

*Duration*.—On the plant 3 to 4 days. Senesced petals drop away cleanly.

*Size*.—Large for a floribunda rose. When open, the average flower diameter is 85-90 mm and the average flower height is 40 mm.

*Form*.—Shape of flower when viewed from the side: Upon opening, upper part: Flattened convex. Upon opening, lower part: Flat. Open flower, upper part: Flat. Open flower, lower part: Concave.

Color:

*Upon opening, petals*.—Outermost petals: Outer Side: Yellow-Orange Group 23B. Inner Side: Yellow-Orange Group 15B. Innermost petals: Outer Side: Orange Group 24C. Inner Side: Yellow Orange Group 16B.

*Upon opening, basal petal spots*.—Basal petal spot, outermost petals: Outer Side: Yellow Group 2A. Inner Side: None observed. Basal petal spot, innermost petals: Outer Side: Yellow Group 2A. Inner Side: Yellow Group 7A.

*After opening, petals*.—Outermost petals: Outer Side: Orange Group 27A. Inner Side: Yellow Group 18C. Innermost petals: Outer Side: Yellow Orange Group 20D. Inner Side: Yellow Group 18C.

*After opening, basal petal spots*.—Basal petal spot, outermost petals: Outer Side: Yellow Group 4A. Inner Side: Yellow Group 2A. Basal petal spot, innermost petals: Outer Side: Yellow Group 6A. Inner Side: None observed.

General tonality: On open flower Yellow-Orange Group 27C. No change in the general tonality at the end of the 3 day. Afterwards, general tonality is Yellow-Orange Group 18B and 18C.

Petals:

*Petal count*.—Very Double.

*Average range*.—Approximately 80 to 90 petals under normal conditions.

*Petal reflex*.—Petals reflex medium to strongly.

*Petal margin*.—Undulated.

*Petal shape*.—Obovate. Apex: Obtuse. Base: Obtuse.

*Petal size*.—20 to 55 mm (l)×15 to 60 mm (w).

*Petal arrangement*.—Rosetted. Texture: Smooth.

Petaloids:

*Petaloid count*.—Average of 15 to 20 per flower.

*Petaloid size*.—10 mm (l)×4 to 7 mm (w).

*Petaloid color*.—Inner side: Yellow-Orange Group 19B. Outer side: Orange group 24C.

*Petaloid texture*.—Smooth.

*Margins*.—Strongly undulated.

*Petaloid shape*.—Most commonly oblancelate to obovate, with some petaloids highly irregular. Apex: Obtuse. Base: Attenuate to obtuse.

Reproductive organs:

*Pistils*.—Average. Approximately 60 present. Stigmas: Location: Inferior in position to anthers. Color: Greyed-Orange Group 163B. Styles: Length: About 5 to 10 mm long. Color: Red Group 46C.

*Stamens*.—Approximately 90 on average and irregularly arranged. Anthers: Size: Average 2 to 3 mm (l)×1 to 2 mm (w). Pollen: Generally present. Color:

Greyed-Yellow Group 163C. Filaments: Color: Yellow-Orange Group 14B. Length: 8 to 14 mm.

*Receptacle*.—Surface: Smooth. Color: Yellow-Green Group 144A. Intonations: Greyed-Purple Group 183A. Shape: Urn-shaped. Texture: Smooth. Size: 10 mm (h)×13 mm (w).

*Pedicel*.—Surface: With stipitate glands. Length: 50 to 70 mm average length. Diameter: 3 to 4 mm average diameter. Color: Yellow-Green Group 144A. Strong intonations of Greyed-Purple Group 184A. Strength: Somewhat strong. Texture: Smooth. Borne: Multiple flower buds per stem, generally 1 to 5. Flowers held upright.

*Peduncle*.—Surface: Smooth. Length: 55 to 80 mm average length. Diameter: 5 to 6 mm average diameter. Color: Yellow-Green Group 144A. Strong intonations of Greyed-Red Group 178A. Strength: Strong. Borne: Multiple flower buds per stem, generally 1 to 5.

THE PLANT

*Growth*.—Vigorous growth.

*Plant habit*.—Upright to bushy. When grown as a field plant, the average plant height is 90 to 120 cm and the average plant width is 75 to 90 cm.

*Stems*.—Stem color: Young wood: Yellow-Green Group 144B. Older wood: Yellow-Green Group 146C. Intonations: Strong intonations of Greyed-Red 178A. Stem surface texture: Young wood: Smooth. Older wood: Rough.

*Prickles*.—Present. Incidence: Average of 3 per each 10 cm of stem. Size: Average length: 9 to 10 mm. Color: Immature prickles: Yellow-Green Group 144D. Mature prickles: Yellow-Green Group 146D. Senescing to Greyed-Brown Group 199C. Shape: Deeply concave. Anthocyanin: Plentiful. Color: Greyed-Purple Group 184A.

*Leaves*.—Normally 5 leaflets on normal leaves in middle of the stem. Venation pattern: Pyramidal net pattern. Leaf size: 150 to 160 mm (l)×110 to 125 mm (w). Abundance: Very.

*Leaflets*.—Size: Average size of the terminal leaflet is 70 to 80 mm (l)×50 to 65 mm (w). Shape: Obtuse. Base: Obtuse. Apex: Acute. Margins: Serrated. Surface: Semi-glossy. Texture: Upper side of leaflet: Leathery. Under side of leaflet: Leathery. Color, mature foliage: Upper Leaflet Surface: Yellow-Green Group 147A. Lower Leaflet Surface: Yellow-Green Group 146B. Color, juvenile foliage: Upper Leaflet Surface: Yellow-Green Group 144A. Lower Leaflet Surface: Yellow-Green Group 146B. Anthocyanin intonation: Greyed-Red Group 178A. Location: Margins and midrib of mature leaflets, widespread on juvenile foliage, especially along veins. Arrangement: Odd pinnate. Venation: Reticulate.

*Stipules*.—Size: 15 to 25 mm (l)×5 to 7 mm (w). Stipule color: Yellow-Green Group 146B. Anthocyanin: Greyed-Purple Group 184A. Stipitate glands: Present on margins. Margins: With stipitate glands. Texture: Smooth. Shape: Apex: Apiculate. Base: Flat.

*Petiole*.—Length: Average 40 to 50 mm. Diameter: Average 2 mm. Petiole color: Yellow-Green Group 144D. Underneath: Yellow-Green Group 145A. Margins: With stipitate glands. Anthocyanin: Greyed-Purple Group 185A, generally on upper side. Limited intonations on the underside. Prickles: Yes. Stipitate Glands: Limited on margins. Texture: Pubescent on upper side, smooth on the underside.

*Petiole rachis*.—Length: Average 20 to 25 mm. Diameter: Average 1 to 2 mm. Color: Yellow-Green Group 144D. Anthocyanin present on upper side and margins: Greyed-Purple Group 185A. Margins: With stipitate glands. Prickles: A few small prickles underneath. Stipitate glands: Limited numbers of stipitate glands on margins.

Hips/seed formation: None observed.

Winter hardiness: To date, the variety has been grown successfully in Zone 7.

Disease resistance: Very good resistance to powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

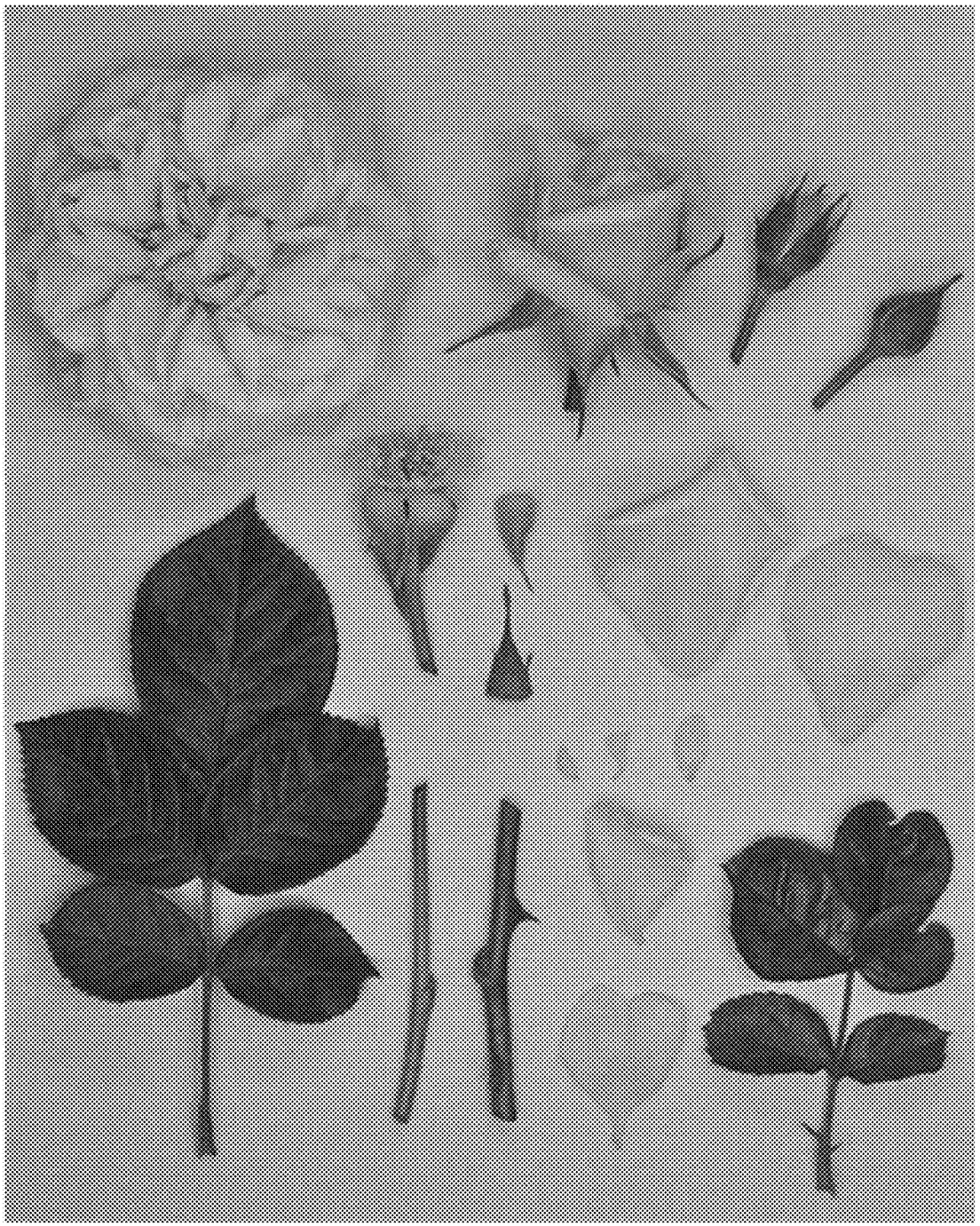

* * * * *